United States Patent [19]

Reuschling et al.

[11] Patent Number: 5,194,619
[45] Date of Patent: Mar. 16, 1993

[54] PROCESS FOR THE PREPARATION OF SUBSTITUTED INDENES

[75] Inventors: Dieter Reuschling, Butzbach; Jürgen Rohrmann, Kelkheim; Gerhard Erker, Münster; Reiner Nolte, Ludwigshafen; Michael Aulbach, Senden-Bösensell; Astrid Weiss, Münster, all of Fed. Rep. of Germany

[73] Assignee: Hoechst Aktiengesellschaft, Frankfurt am Main, Fed. Rep. of Germany

[21] Appl. No.: 837,367

[22] Filed: Feb. 14, 1992

[30] Foreign Application Priority Data

Feb. 18, 1991 [DE] Fed. Rep. of Germany ....... 4104931

[51] Int. Cl.$^5$ .................. C07D 213/24; C07D 333/06
[52] U.S. Cl. ...................... 546/348; 549/59; 549/60; 549/78; 549/80; 549/497; 549/502; 549/504; 549/505; 546/285; 546/284; 546/339; 546/346; 556/489; 568/632; 568/633; 568/634; 570/127; 570/129; 585/422; 585/425; 585/358
[58] Field of Search ...................... 549/78, 80, 59, 60, 549/497, 502, 504, 505; 546/213, 284, 339, 346, 348; 556/489; 568/632, 633, 634; 570/127, 129; 585/422, 425, 407, 408, 410, 358

[56] References Cited

U.S. PATENT DOCUMENTS

3,210,433 10/1965 Chibnik .............................. 585/409
4,667,238 6/1987 Pedersen et al. .................... 260/668

FOREIGN PATENT DOCUMENTS

0129368 6/1984 European Pat. Off. .
0316155 11/1988 European Pat. Off. .
0351392 1/1990 European Pat. Off. .

OTHER PUBLICATIONS

Criegee, R. et al, *Chem. Ber.* 97; 3461–3468 (1964).
Maréchal, E. et al, *Bull. Soc. Chim. Fr.* 6:1981–1989 (1969).
Maréchal, E. et al, *Bull. Soc. Shim. Fr.* 6:2039–2044 (1969).
Cedheim, L. et al, *Acta Chem. Scand. B* 30:527–532 (1976).
Miyamoto, T. K. et al, *Chem. Lett.*:729–730 (1981).
Mise, T. et al, *Chem. Lett.*:1853–1856 (1989).
Soga, K., et al, *Macromol.* 22:3824–3826 (1989).
Spaleck, W., et al, *New J. Chem.* 14:499–503 (1990).
Mallin, D. T., et al., *J. Am. Chem. Soc.* 112:2030–2031 (1990).
Roll, V. W., et al, *Angew. Chem.* 102:339–341 (1990).

*Primary Examiner*—Glennon H. Hollrah
*Assistant Examiner*—Mark W. Russell

[57] ABSTRACT

The compounds of the formula I or Ia

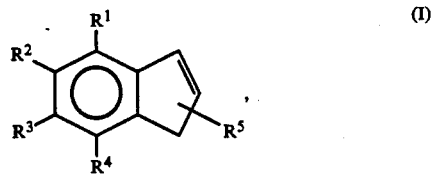

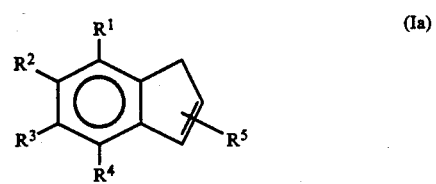

in which
$R^1$ is alkyl, aryl, alkoxy, alkenyl, arylalkyl, alkylaryl, aryloxy, fluoroalkyl, halogenoaryl, alkynyl, trialkylsilyl or a heteroaromatic radical,
$R^2$, $R^3$ and $R^4$, in addition to hydrogen, have the meanings given under $R^1$ and
$R^5$ is hydrogen, alkyl, fluoroalkyl or alkenyl, can be obtained in a one-stage process by reaction of a compound II

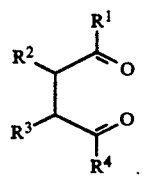

with (substituted) cyclopentadiene in the presence of a base. The compounds I and Ia are suitable as ligands for metallocene complexes which are used as catalysts in olefin polymerization.

5 Claims, No Drawings

PROCESS FOR THE PREPARATION OF SUBSTITUTED INDENES

The present invention relates to a process for the one-stage preparation of substituted indenes.

Compounds of this type are advantageously suitable as ligand systems for the preparation of chiral, stereorigid metallocene complexes. The corresponding zirconium derivatives in particular are of importance as highly active catalysts in olefin polymerization (cf. EP-A 129,368). The catalyst properties can be influenced in a specific manner by varying the ligand system, for example by substitution. It is possible by this means to change the polymer yield, the molecular weight, the tacticity or the melting point of the polymers to the desired extent (New J. Chem. 14 (1990) 499; J. Am. Chem. Soc. 112 (1990) 2030; Angew. Chem. 102 (1990) 339; Chem. Lett. (1989) 1853; EP-A 316,155; and EP-A 351,392).

Indenes can furthermore also be employed as monomers in homopolymerization or copolymerization with other olefins, such as, for example, styrene (cf. Macromol. 22 (1989) 3824; Bull. Soc. Chim. Fr. 6 (1969) 2039).

However, the few indenes substituted by six-membered rings which are described in the literature are as a rule accessible only in low yields via multi-stage syntheses. These indene derivatives are usually prepared by fusing the five-membered ring onto a correspondingly substituted aromatic in about 5 synthesis stages. Certain substitution patterns are not accessible by this route (Bull. Soc. Chim. Fr. (1969), 6, 1981-89; Acta Chem. Scand. B 30 (1976) 527-32; Austr. J. Chem. 29 (1970) 2572; Chem. Lett. (1981) 729-730; and Ber. 97 (12), (1964) 3461-8).

There was thus the object of discovering a process for the preparation of the abovementioned indenes which avoids the disadvantages known from the prior art.

According to the invention, this object is achieved by reacting cyclopentadienes with diketones or ketoaldehydes to give the desired substituted indenes in a one-stage process which is easy to manage industrially. At the same time, the process according to the invention allows the preparation of novel compounds of the structural type mentioned.

The present invention therefore relates to a process for the preparation of a compound of the formula I or an isomer thereof of the formula Ia

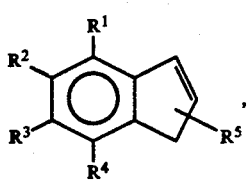

(I)

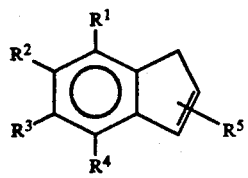

(Ia)

in which $R^1$ is $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl, a radical $-SiR^6_3$ or a heteroaromatic radical having 5 or 6 ring members, which can contain one or more hetero atoms, $R^2$, $R^3$ and $R^4$ are identical or different and, in addition to hydrogen, have the meanings given for $R^1$, $R^5$ is hydrogen, $(C_1-C_{10})$alkyl, $(C_1-C_{10})$fluoroalkyl or $(C_2-C_{10})$alkenyl and $R^6$ is $(C_1-C_{10})$alkyl, which comprises reacting a compound of the formula II

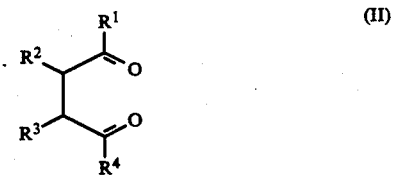

(II)

with a compound of the formula III

(III)

the substituents $R^1-R^5$ having the meanings given, in the presence of a base.

Alkyl is straight-chain or branched alkyl. Halogen is fluorine, chlorine, bromine or iodine, in particular fluorine or chlorine. Examples of heteroaromatic radicals are thiophenyl, furyl and pyridyl.

Preferably, in the formulae I and Ia, $R^1$ is $(C_1-C_{10})$alkyl, phenyl, $(C_1-C_4)$alkoxy, $(C_2-C_6)$alkenyl, $(C_7-C_{10})$arylalkyl $(C_7-C_{10})$alkylaryl, phenoxy, $(C_1-C_6)$fluoroalkyl, halogenophenyl, $(C_2-C_6)$alkynyl, a radical $—SiR^6_3$, or a heteroaromatic radical having 5 or 6 ring members, which can contain one or more oxygen, sulfur and/or nitrogen atoms, $R^2$, $R^3$ and $R^4$ are identical or different and, in addition to hydrogen, have the meanings given for $R^1$, $R^5$ is hydrogen, $(C_1-C_6)$alkyl, $(C_1-C_6)$fluoroalkyl or $(C_2-C_6)$alkenyl and $R^6$ is $(C_1-C_6)$alkyl.

In particular, $R^1$ is $(C_1-C_{10})$alkyl, phenyl, $C_2$-alkenyl, $(C_7-C_{10})$arylalkyl, $(C_7-C_{10})$alkylaryl, $(C_1-C_6)$fluoroalkyl, halogenophenyl, a radical $—SiR^6_3$ or a heteroaromatic radical having 5 or 6 ring members, which contains an oxygen, sulfur or nitrogen atom, $R^2$, $R^3$ and $R^4$ are identical or different and, in addition to hydrogen, have the meanings given for $R^1$, $R^5$ is hydrogen, $(C_1-C_3)$alkyl, $(C_1-C_3)$fluoroalkyl or $(C_2-C_3)$alkenyl and $R^6$ is methyl or ethyl.

The preparation of the starting compounds II is known from the literature (diketones: Chem. Ber. 114, 1226 (1981), ibid. 109, 3426 (1976), and ibid. 107, 2453 (1974); ketoaldehydes: Synthesis 1985, 1058).

The cyclopentadienes III are commercially obtainable or can be prepared by known methods, for example by alkylation on the cyclopentadiene anion.

The substituted indenes are obtained as double-bond isomers (I/Ia, cf. Table 1). If a substituted cyclopentadiene III ($R^5 \neq H$) is employed, constitution isomers can additionally be formed, which can be separated by column chromatography. The double-bond isomers (mixture) can be employed directly for synthesis of the corresponding metallocene complexes; constitution isomers are to be separated before the subsequent reaction.

The reaction is carried out in an inert solvent. Alcohols such as methanol, ethanol or t-butanol, in particular methanol, are preferably used.

A large number of compounds can be used as bases for the process according to the invention. Examples which may be mentioned are: alkali metal and alkaline earth metal hydroxides, alkali metal and alkaline earth metal alcoholates, such as sodium methanolate, sodium ethanolate and potassium tert-butylate, amides, such as lithium diisopropylamide, or amines. Of these compounds, sodium methanolate, potassium tert-butylate and potassium hydroxide are preferred.

The molar ratios of the starting compounds, including the base to be used, can vary within wide limits. The molar ratio of compound II:III:base is preferably 1:1–1.5:2–3; in particular 1:1.1:2.5.

The reaction temperature is preferably −40° C. to 100° C., in particular 0° C.–25° C.

The reaction times as a rule vary between 10 minutes and 100 hours, preferably between 1 hour and 30 hours.

A mixture of the compounds II and III—if appropriate in a solvent—is preferably added to the initial solution consisting of base and solvent.

A distinctive feature of the process according to the invention is that the aromatic six-membered ring of the substituted indene matrix is built up in one reaction step, so that a large number of different substitution patterns can be realized very easily, these being accessible only with difficulty, if at all, by the conventional route.

The following examples serve to illustrate the invention in more detail.

General comments: The organometallic compounds were prepared and handled with exclusion of air and moisture under the protection of argon (Schlenk technique). All of the solvents required were rendered absolute before use by boiling for several hours over a suitable desiccant and subsequent distillation under argon. The diketones and ketoaldehydes employed as starting compounds were prepared by methods known from the literature. Cyclopentadiene and methylcyclopentadiene were obtained by cracking the dimers and were stored at −35° C.

EXAMPLE 1

4,7-Dimethylindene (1)

34.4 g (1.50 mol) of sodium were dissolved in 300 ml of absolute methanol. A mixture of 53.8 ml (43.6 g, 0.66 mol) of cyclopentadiene and 67.3 g (0.59 mol) of 2,5-hexanedione was slowly added dropwise at 0° C. When the addition had ended, the mixture was stirred at 0° C. for a further hour and then at room temperature for a further two hours. 200 ml of water and 300 ml of diethyl ether were added to the reaction mixture. The organic phase was separated off in a separating funnel and the aqueous phase was washed twice with 50 ml of diethyl ether each time. The combined organic phases were washed twice with 50 ml of water each time and then dried over sodium sulfate. The solvent was removed in vacuo and the oily residue was subjected to fractional distillation (48°–52° C., 0.1 torr). Yield 48.8 g (56 %). For the NMR data, see Table 1.

EXAMPLE 2

4,7-Dimethylindene (1)

23 g (1.0 mol) of sodium were dissolved in 250 ml of absolute methanol. A mixture of 45.6 g (0.40 mol) of 2,5-hexanedione and 39.7 g (0.60 mol) of cyclopentadiene was added dropwise at 0° C. in the course of 1–2 hours. After stirring at room temperature for 1 hour, 50 ml of $H_2O$ were added to the dark brown solution. The organic phase was diluted with about 1 l of diethyl ether. The aqueous phase was separated off. The organic phase was dried over sodium sulfate and evaporated. The oil which remained was chromatographed on silica gel 60. 44.2 g (76%) of the indene 1 could be eluted with hexane/methylene chloride (10:1), and is obtained as a colorless to pale yellow oil after the mobile phase has been stripped off under an oil pump vacuum. For the NMR data, see Table 1.

EXAMPLE 3

4-Methyl-7-(1-propyl)indene (2)

45 ml of a 30 percent strength solution of sodium methanolate in methanol (250 mmol) were initially introduced into the reaction vessel at 0° C., and a mixture of 14.2 g (100 mmol) of 2,5-octanedione and 9 ml (110 mmol) of cyclopentadiene was added in the course of 30 minutes. After the mixture had been stirred at room temperature for 3 hours, it was poured into 300 ml of ice-water and extracted with diethyl ether and the organic phase was dried over magnesium sulfate. The residue which remained after evaporation was chromatographed on silica gel. 6.8 g (39%) of the indene 2 could be isolated with hexane as the mobile phase.

For the NMR data, see Table 1.

EXAMPLE 4

The procedure was analogous to Example 3. 250 mmol of potassium tert-butylate in 50 ml of methanol were used as the base. 7.2 g (42 %) of the indene 2 were isolated.

EXAMPLE 5

The procedure was analogous to Example 3. 250 mmol of potassium hydroxide powder in 50 ml of methanol were used as the base. 9.0 g (52 %) of the indene 2 were isolated.

EXAMPLE 6

4-Ethyl-7-(1-pentyl)indene (3)

A mixture of 17.0 g (100 mmol) of 2,5-decanedione and 9.0 ml (110 mmol) of cyclopentadiene was added to a solution of 28.0 g (250 mmol) of potassium tert-butylate in 50 ml of methanol at 0° C. in the course of 20 minutes. After the solution had been stirred at 0° C. for 3 hours and at room temperature for a further 2 hours, water was added and the mixture was extracted with methylene chloride. After drying over magnesium sulfate, the organic phase was evaporated and the residue was chromatographed on silica gel.

12.5 g (62 %) of the indene 3 could be isolated with hexane as the mobile phase.

For the NMR data, see Table 1.

EXAMPLE 7

4-Methyl-7-(1-hexyl)indene (4)

3.5 g (0.15 mol) of sodium were dissolved in 100 ml of dry methanol and the solution was cooled to 0° C. A mixture of 12.8 g (0.06 mol) of undecanedione and 5 ml (4.0 g, 0.06 mol) of cyclopentadiene was added dropwise to the solution. After the mixture had been stirred at 0° C. for a further hour and at room temperature for 2 days, it was hydrolyzed with 300 ml of water and extracted twice with 100 ml portions and twice with 50 ml portions of petroleum ether. The combined organic phases were dried over $MgSO_4$ and concentrated to dryness and the residue was taken up in about 30 ml of methanol.

4 precipitated in cubic crystals at −20° C., and these liquefied at room temperature to give a yellow oil. Yield 5.3 g (44 %). Two isomers were prepared in a ratio of 5:3;

IR (film): $\nu=2955-2857$ (n-$CH_2$, $CH_3$), 1456, 1457, 1379, 1026, 1020, 813 (2 adjacent aromatic C-H). MS (70 eV): m/z (%) =129 (methylindene, 80), 115 (indenyl, 77), 91 (tropylium, 34), 77 (phenyl, 33).

$C_{16}H_{22}$ (214.35) calculated C 89.65 H 10.35 found C 87.90 H 10.17

For the NMR data, see Table 1.

EXAMPLE 8

4-Methyl-7-(1-octyl)indene (5)

9 ml (110 mmol) of cyclopentadiene were added to a solution of 28.0 g (250 mmol) of potassium t-butylate in 50 ml of methanol at 0° C. 21.2 g (100 mmol) of 2,5-tridecanedione were then added dropwise at 0° C. After the mixture had been stirred at 0° C. for 1 hour, it was stirred at room temperature for a further 3 hours. Working up was carried out analogously to Example 6. Column chromatography gave 16.9 g (70 %) of the indene 5.

For the NMR data, see Table 1.

EXAMPLE 9

4-Methyl-7-(2-propyl)indene (6)

14.2 g (100 mmol) of 2-methyl-3,6-heptanedione were reacted analogously to Example 6. Column chromatography gave 13.7 g (80 %) of the indene 6. For the NMR data, see Table 1.

EXAMPLE 10

4-Methyl-7-(2-phenylethyl)indene (7)

20.4 g (100 mmol) of 1-phenyl-3,6-heptanedione were reacted analogously to Example 6. Column chromatography gave 11.2 g (48 %) of the indene 7. For the NMR data, see Table 1.

EXAMPLE 11

4-Methyl-7-phenylindene (8)

5 g (0.21 mol) of sodium were dissolved in 100 ml of methanol in a Schlenk tube and the solution was cooled to 0° C. A mixture of 15.8 g (0.84 mol) of 1-phenyl-1,4-pentanedione and 7.3 ml (5.8 g, 0.08 mol) of cyclopentadiene was added dropwise in the course of 15 minutes. The red solution was stirred at room temperature overnight, hydrolyzed with 200 ml of water and extracted five times with 75 ml of petroleum ether each time. The combined organic extracts were filtered and concentrated to dryness and the residue was subjected to fractional distillation.

Yield 10.2 g (50 %) of a red oil, boiling point 135° C. For the NMR data, see Table 1.

IR (film): $\nu=3026$ $cm^{-1}$, 2916, 1479, 818, 772, 763, 750, 698.

$C_{16}H_{14}$ (206.288) calculated C 93.16 H 6.84 found C 93.47 H 7.07

EXAMPLE 12

7-Diphenylindene (9)

18.9 ml (105 mmol) of a 30 percent strength sodium methanolate solution and 3.8 ml (46 mmol) of cyclopentadiene were added to a solution of 10.0 g (42 mmol) of 1,2-dibenzoylethane in 10 ml of methanol at 0° C. After the mixture had been stirred at 0° C. for 1.5 hours and at room temperature for 6 hours, it was hydrolyzed and extracted with methylene chloride. The organic phase was dried and evaporated. The residue was chromatographed on silica gel. 3.81 g (34 %) of the indene 9 could be isolated with a mobile phase mixture of methylene chloride/hexane (1:1).

For the NMR data, see Table 1.

EXAMPLE 13

The procedure was as in Example 12. However, potassium t-butylate (105 mmol) in methanol was used as the base. 32.9 g (35 %) of the indene 9 were obtained after column chromatography.

EXAMPLE 14

4,7-Di-tert-butylindene (10)

A mixture of 14.8 g (74.6 mmol) of 2,2,7,7-tetramethyl-3,6-octanedione and 6.7 ml (82.1 mmol) of cyclopentadiene was added to 34.3 ml of a 30 percent strength solution of sodium methanolate (186 mmol) in methanol at 0° C. in the course of 10 minutes. After the mixture had been stirred at room temperature for 30 hours, it was hydrolyzed and extracted with methylene chloride. After drying over $MgSO_4$, the product was evaporated to dryness. Column chromatography on silica gel with hexane as the mobile phase gave 1.75 g (10 %) of the indene 10. For the NMR data, see Table 1.

EXAMPLE 15

The procedure was as in Example 14. However, 13.4 ml (164.2 mmol) of cyclopentadiene were employed. 1.95 g (11.5%) of the indene 10 were obtained after column chromatography.

EXAMPLE 16

4-Methyl-7-(p-chlorophenyl)indene (11)

21.1 g (100 mmol) of 1-(p-chlorophenyl)-1,4-pentanedione were reacted analogously to Example 8. Column chromatography with hexane/methylene chloride (10:1) as the mobile phase and subsequent recrystallization from hot methanol gave 15.6 g (65 %) of the indene 11.

For the NMR data, see Table 1.

EXAMPLE 17

4-Methyl-7-(3-pyridyl)indene (12)

17.7 g (100 mmol) of 1-(3-pyridyl)-1,4-pentanedione were reacted analogously to Example 6. Column chromatography with ethyl acetate as the mobile phase gave 9.98 g (48 %) of the indene 12.

EXAMPLE 18

4-Methyl-7-(2-furyl)indene (13)

16.6 g (100 mmol) of 1-(2-furyl)-1,4-pentanedione were reacted analogously to Example 8. Column chromatography with hexane/methylene chloride (7:1) as the mobile phase gave 13.7 g (70 %) of the indene 13. For the NMR data, see Table 1.

EXAMPLE 19

4,7-Bis(2-furyl)indene (14)

18.9 ml of a 30 percent strength solution of sodium methanolate (105 mmol) in methanol was initially introduced into the reaction vessel at 0° C, and a solution of 9.2 g (42.2 mmol) of 1,4-bis(2-furyl)-1,4-butanedione and 3.8 ml (46.2 mmol) of cyclopentadiene in DMSO were added dropwise in the course of 1 hour. After the mixture had been stirred at room temperature for 45 minutes it was poured onto ice-water and extracted with diethyl ether. After drying and evaporation, the residue was chromatographed on silica gel. 3.0 g (29 %) of the indene 14 could be obtained with hexane/methylene chloride (2:1) as the mobile phase.

For the NMR data, see Table 1.

EXAMPLE 20

4,7-Bis(2-thiophene) indene (15)

14.7 ml of a 30 percent strength solution of sodium methanolate (81.7 mmol) in methanol were initially introduced into the reaction vessel at 0° C, and a solution of 8.15 g (32.6 mmol) of 1,4-bis(2-thiophene)-1,4-butanedione and 2.9 ml (35.4 mmol) of cyclopentadiene in DMSO was added dropwise in the course of 1 hour. After the mixture had been stirred for 2 hours it was poured onto 300 ml of ice-water, extracted with diethyl ether, dried and evaporated. Column chromatography with hexane/methylene chloride (2:1) as the mobile phase gave 3.3 g (36%) of the indene 15.

For the NMR data, see Table 1.

EXAMPLE 21

4-Ethylindene (16)

49.9 ml (250 mmol) of a 30 percent strength solution of sodium methanolate in methanol were initially introduced into the reaction vessel at 0° C., and a mixture of 13.2 g (100 mmol) of 4-oxocapronaldehyde hydrate and 9.0 ml (110 mmol) of cyclopentadiene, dissolved in 5 ml of methanol, was added in the course of 30 minutes. After the mixture had been stirred at 0° C. for 2 hours and at room temperature for 2.5 hours, it was hydrolyzed and extracted with methylene chloride. The organic phase was dried over MgSO$_4$ and concentrated. Column chromatography with hexane/diisopropyl ether (100:1) gave 5.97 g (41%) of the indene 16.

For the NMR data, see Table 1.

EXAMPLE 22

4-(1-Heptyl)indene (17)

20.4 ml of a 30 percent strength solution of sodium methanolate (111 mmol) in methanol were initially introduced into the reaction vessel at 0° C., and a mixture of 9.0 g (44.5 mmol) of 4-oxoundecylaldehyde and 4.0 ml (49 mmol) of cyclopentadiene was added in the course of 30 minutes. After the mixture had been stirred at 0° C. for 2 hours and at room temperature for a further 3 hours, it was hydrolyzed, methylene chloride was added and the mixture was filtered over Corolite. The organic phase was separated off, dried over MgSO$_4$ and evaporated. Column chromatography with hexane as the mobile phase gave 3.2 g (34%) of the indene 17. For the NMR data, see Table 1.

EXAMPLE 23

1-(2,4,4-Trimethylpentyl)indene (18)

19.1 ml of a 30 percent strength solution of sodium methanolate (106 mmol) in methanol were initially introduced into the reaction vessel at 0° C., and a mixture of 8.4 g (42.4 mmol) of 4-oxo-6,8,8-trimethylnonylaldehyde and 3.8 ml (46.5 mmol) of cyclopentadiene was added in the course of 20 minutes. After the mixture had been stirred at room temperature for 4.5 hours, it was poured onto 150 ml of ice-water and extracted with diethyl ether. The organic phase was dried and evaporated. Column chromatography with hexane as the mobile phase gave 4.6 g (48%) of the indene 18.

For the NMR data, see Table 1.

EXAMPLE 24

5,7-Diphenyl-4-(2-furyl)indene (19)

3.5 g (0.15 mol) of sodium were dissolved in 100 ml of methanol and the solution was cooled to 0° C. A mixture of 20.0 g (0.06 mol) of 1-furyl-2,4-phenyl-1,4-butanedione and 5.0 ml (4.0 g, 0.06 mol) of cyclopentadiene in 100 ml of THF was added dropwise at 0° C. in the course of 30 minutes. The suspension was stirred at 0° C. for a further 1 hour and at room temperature for 2 days. The dark red solution was hydrolyzed with 300 ml of water, during which 19 already precipitated as a pale brown solid. The reaction mixture was extracted twice with 100 ml and twice with 50 ml of petroleum ether, the organic phases were dried over MgSO$_4$, the solvent was distilled off and the residue was taken up in 200 ml of methanol. Further product crystallized out at −20° C.

Yield 13.4 g (67 %), melting point 134° C. MS (70 eV): m/z (%)=334 (M+, 39), 257 (M+-phenyl, 37), 143 (phenylfuryl, 100), 113 (indenyl, 69), 77 (phenyl, 41). IR (KBr): ν3050 cm$^{-1}$, 2963, 2924, 2889 (CH$_2$, valency), 1261, 1094, 1027, 1012, 803 (2 adjacent aromatic C-H), 768, 733 (5 adjacent aromatic C-H), 708, 702, 686.

C$_{25}$H$_{18}$O (334.42) calculated C 89.79 H 5.43 found C 89.27 H 5.48

EXAMPLE 25

2,4,7- and 3,4,7-Trimethylindene (20) and (21)

11.5 g (0.52 mol) of sodium were dissolved in 150 ml of absolute methanol and the solution was then heated to 55° C. A mixture of 18.3 g (0.25 mol) of methylcyclopentadiene and 28.5 g (0.25 mol) of 2,5-hexanedione was slowly added dropwise. When the addition had ended, the mixture was stirred at 55° C. for a further two hours and then hydrolyzed at room temperature with 100 ml of water. After addition of 150 ml of diethyl ether, the organic phase was separated off in a separating funnel and the aqueous phase was washed twice with 50 ml of diethyl ether. The combined organic phases were dried over sodium sulfate, the solvent was then removed in vacuo and the oily residue was subjected to fractional distillation. The fraction at 58°–67° C. (0.1 torr) contained an isomer mixture of 2,4,7- and 3,4,7-trimethylindene (20, 21) in a ratio of 3:10.

Yield 7.3 g (19 %).

For the NMR data, see Table 1.

EXAMPLE 26

A mixture of 12 g (150 mmol) of methylcyclopentadiene and 17.1 g (150 mmol) of 2,5-hexanedione was added dropwise at 0° C. to a solution of 8.6 g (375 mmol) of sodium in 200 ml of methanol in the course of 1 hour. After stirring at room temperature for 18 hours, the dark red mixture was poured onto ice-water and extracted with ether. After drying over $Na_2SO_4$, the solvent was stripped off and the oil which remained was chromatographed on 600 g of silica gel (long column). First 3.0 g (13 %) of 3,4,7-trimethylindene (21) and then 1.5 g (6 %) of 2,4,7-trimethylindene (20) could be eluted, closely following one another, with hexane as the mobile phase. Subsequent recrystallization from hexane gave the pure products. For the NMR data, see Table 1.

EXAMPLE 27

10.0 g (125 mmol) of methylcyclopentadiene were first added dropwise at 0° C. to a solution of 6.4 g (280 mmol) of sodium in 100 ml of methanol. This mixture was added dropwise at room temperature to a solution of 13.1 ml (112 mmol) of 2,5-hexanedione in 50 ml of methanol in the course of 1 hour. After the mixture had been stirred at room temperature for 4 hours, it was poured onto ice-water and acidified to pH 2. Hereafter, it was extracted with diethyl ether, dried over $Na_2SO_4$ and evaporated. The residue was chromatographed on 600 g of silica gel (long column) with hexane/methylene chloride (20:1). 0.90 g (5 %) of 3,4,7-trimethylindene (21) and 0.4 g (2%) of 2,4,7-trimethylidene (20) were obtained. For the NMR data, see Table 1.

EXAMPLE 28

A mixture of 12.8 g (112 mmol) of 2,5-hexanedione and 10.0 g (125 mmol) of methylcyclopentadiene was added at 0° C. to a solution of 32.0 g (280 mmol) of potassium tertbutylate in 300 ml of methanol in the course of 1 hour. After the mixture had been stirred at room temperature for 10 hours, it was poured onto HCl-acid ice-water and extracted several times with diethyl ether. The residue which remained after drying and concentration was chromatographed on 200 g of silica gel. The two isomers 20 and 21 were eluted together, with hexane/methylene chloride (10:1) as the mobile phase. Yield 4.0 g (23%). Isomer ratio 20:21=1:3.

TABLE 1

$^1$H-NMR data of the compounds 1-21($CDCl_3$, 100 and 200 MHz)

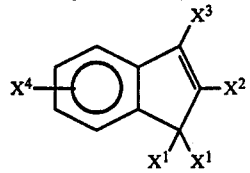

(The symbols "X" serve merely to allocate the signals measured to particular substituents)

| Compound No. | $X^1$ | $X^2$ | $X^3$ | $X^4$ | Others |
|---|---|---|---|---|---|
| 1 | 3.49s | 6.78dt | 7.23m | 7.25d;7.15d | 2.68s, 2.57s($CH_3$) |
| 2(2isomers, 5:3) | 3.25t, 3.30t | 6.5m | 7.0m | 7.0m | 2.45s;2.30s($CH_3$), 2.5–2.8m, 1.40–1.85m, 0.85–1.0m, (n-$C_3H_7$) |
| 3(2isomers, 5:3) | 3.25t, 3.30t | 6.5m | 7.0m | 7.0m | 2.40s, 2.30s($CH_3$), 2.52–2.82m, 0.75–1.80m (n-$C_5H_{11}$) |
| 4(2isomers, 5:3) | 3.32t, 3.39t | 6.59m | 6.95m | 7.05m | 2.47s, 2.37s($CH_3$), 3.22t, 3.39t, 2.77t, 2.70t, 1.66m, 1.35m, 0.93m(n-$C_6H_{13}$) |
| 5(2isomers, 5:3) | 3.25t, 3.30t | 6.5m | 7.0m | 7.0m | 2.40s, 2.30s($CH_3$), 2.5–2.8m, 0.75–1.80m (n-$C_8H_{17}$) |
| 6(2isomers, 5:3) | 3.25t, 3.35t | 6.5m | 7.0m | 7.0m | 2.40s, 2.30s($CH_3$), 3.1m, 1.30d, 1.22d (i-$C_3H_7$) |
| 7(2isomers, 4:3) | 3.25m | 6.55m | 7.0m | 7.0m | 2.42s, 2.32s($CH_3$), 2.95m($C_2H_4$), 7.20m($C_6H_5$) |
| 8(2isomers) | 3.59t, 2.62t | 6.63m | 7.0m | 7.0–7.5m | 7.0–7.5m($C_6H_5$) |
| 9 | 3.55t | 6.57dt | 7.10dt | 7.2–7.6m | 7.2–7.6m($C_6H_5$) |
| 10 | 3.55t | 6.55dt | 7.32dt | 7.17m | 1.42s(t-$C_4H_9$), |
| 11(2isomers, 4:1) | 3.35t, 3.45t | 6.60m | 7.0m | 7.0–7.4m | 7.0–7.4m($C_6H_4Cl$), 2.50s, 2.40s($CH_3$), |
| 12(2isomers, 8:3) | 3.35t, 3.45t | 6.62m | 7.0m | 7.0–7.4m | 2.47s, 2.40s($CH_3$), 8.75m, 8.57dd, 7.85m, 7.75m, 7.1m($C_5H_4N$) |
| 13(2isomers, 4:3) | 3.60t, 3.30t | 6.6m | 7.0–7.4m | 7.0–7.4m | 2.45s, 2.35s($CH_3$), 7.0–7.6m, 6.5m($C_4H_3O$) |
| 14 | 3.65t | 6.7m | 7.4m | 7.4–7.6m | 7.4–7.6m, 6.5m($C_4H_3O$) |
| 15 | 3.70t | 6.65dt | 7.0–7.5m | 7.0–7.5m | 7.0–7.5m($C_4H_3S$) |
| 16(2isomers, 7:4) | 3.35t, 3.27t | 6.50dt | 6.85dt | 6.9–7.3m | 2.75m, 1.25t($C_2H_5$) |
| 17(2isomers, 1:1) | 3.37b, 3.30t | 6.50dt | 6.85dt | 7.0–7.4m | 2.6m, 1.1–1.8m, 0.7m(n-$C_7H_{15}$), |
| 18(2isomers, 1:1) | 3.40t, 3.32t | 6.50dt | 6.87dt | 7.0–7.4m | 1.0–2.90m($CH_2,CH$), 0.9m($CH_3$) |
| 19(2isomers, 3:4) | 3.67m, 3.56m | 5.9m | 6.65m | 7.2–7.5m | 7.2–7.6m($C_6H_5$), 7.2–7.6m, 7.11m, 7.09m, 6.31m($C_4H_3O$) |
| 20 | 3.28m | — | 6.68m | 6.96m | 2.46s, 2.44s, 2.43s($CH_3$) |
| 21 | 3.21m | 6.25m | — | 7.04d, 7.02d | 2.66s, 2.45s, 2.40s($CH_3$) |

We claim

1. A process for the preparation of a compound of the formula I or an isomer thereof of the formula Ia

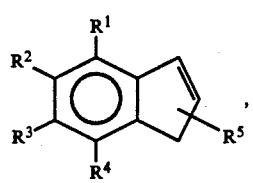

(I)

-continued

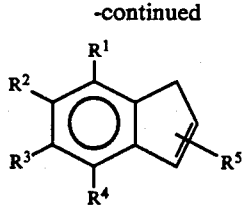
(Ia)

in which

R$^1$ is (C$_1$-C$_{20}$)alkyl, (C$_6$-C$_{14}$)aryl, (C$_1$-C$_{10}$)alkyoxy, (C$_2$-C$_{10}$)alkenyl, (C$_7$-C$_{20}$)arylalkyl, (C$_7$-C$_{20}$)alkylaryl, (C$_6$-C$_{10}$)aryloxy, (C$_1$-C$_{10}$)-fluoroalkyl, (C$_6$-C$_{10}$)halogenoaryl, (C$_2$-C$_{10}$)-alkynyl, a radical —SiR$^6{}_3$ or a heteroaromatic radical having 5 or 6 ring members, which can contain one or more hetero atoms, R$^2$, R$^3$ and R$^4$ are identical or different and, in addition to hydrogen, have the meanings given for R$^1$, R$^5$ is hydrogen, (C$_1$-C$_{10}$)alkyl, (C$_1$-C$_{10}$)fluoroalkyl or (C$_2$-C$_{10}$)alkenyl and R$^6$ is (C$_1$-C$_{10}$)alkyl, which comprises reacting a compound of the formula II

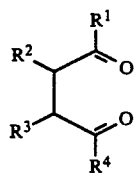
(II)

with a compound of the formula III

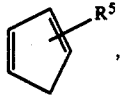
(III)

the substituents R$^1$-R$^5$ having the meanings given, in the presence of a base.

2. The process as claimed in claim 1, wherein, in formula I or formula Ia,

R$^1$ is (C$_1$-C$_{10}$)alkyl, phenyl, (C$_1$-C$_4$)alkoxy, (C$_2$-C$_6$)alkenyl, (C$_7$-C$_{10}$)arylalkyl (C$_7$-C$_{10}$) alkylaryl, phenoxy, (C$_1$-C$_6$)fluoroalkyl, halogenophenyl, (C$_2$-C$_6$)alkynyl, a radical —SiR$^6{}_3$, or a heteroaromatic radical having 5 or 6 ring members, which can contain one or more oxygen, sulfur and/or nitrogen atoms, R$^2$, R$^3$ and R$^4$ are identical or different and, in addition to hydrogen, have the meanings given for R$^1$, R$^5$ is hydrogen, (C$_1$-C$_6$)alkyl, (C$_1$-C$_6$)fluoroalkyl or (C$_2$-C$_6$)alkenyl and R$^6$ is (C$_1$-C$_6$)alkyl.

3. The process as claimed in claim 1, wherein, in formula I or formula Ia,

R$^1$ is (C$_1$-C$_{10}$)alkyl, phenyl, C$_2$-alkenyl, (C$_7$-C$_{10}$)arylalkyl, (C$_7$-C$_{10}$)alkylaryl, (C$_1$-C$_8$)-fluoroalkyl, halogenophenyl, a radical —SiR$^6{}_3$ or a heteroaromatic radical having 5 or 6 ring members, which contains an oxygen, sulfur or nitrogen atom, R$^2$, R$^3$ and R$^4$ are identical or different and, in addition to hydrogen, have the meanings given for R$^1$, R$^5$ is hydrogen, (C$_1$-C$_3$)alkyl, (C$_1$-C$_3$)fluoroalkyl or (C$_2$-C$_3$)alkenyl and R$^6$ is methyl or ethyl.

4. The process as claimed in claim 1, wherein sodium methanolate, potassium tert-butylate or potassium hydroxide is used as the base.

5. The process as claimed in claim 1, wherein the molar ratio of the starting compounds II:III:base is 1:1–1.5:2–3.

* * * * *